(12) United States Patent
Yamagishi et al.

(10) Patent No.: US 7,978,890 B2
(45) Date of Patent: Jul. 12, 2011

(54) APPARATUS AND METHOD OF DISPLAYING IMAGE SCANNING REPORT

(75) Inventors: Hiromasa Yamagishi, Otawara (JP); Kenichi Niwa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1084 days.

(21) Appl. No.: 11/684,740

(22) Filed: Mar. 12, 2007

(65) Prior Publication Data

US 2007/0237375 A1    Oct. 11, 2007

(30) Foreign Application Priority Data

Mar. 23, 2006  (JP) ................................. 2006-080859

(51) Int. Cl.
*G06K 9/00* (2006.01)
*G06Q 10/00* (2006.01)
(52) U.S. Cl. ................................. 382/128; 705/2; 705/3
(58) Field of Classification Search .................. 382/128; 705/2, 3
See application file for complete search history.

(56) References Cited

U.S. PATENT DOCUMENTS

| 6,609,135 | B1 * | 8/2003 | Omori et al. ........................... 1/1 |
| 2004/0249291 | A1 * | 12/2004 | Honda et al. ................... 600/476 |
| 2005/0147284 | A1 * | 7/2005 | Vining et al. ................... 382/128 |
| 2005/0283387 | A1 * | 12/2005 | Donoghue et al. ................ 705/3 |
| 2007/0081240 | A1 * | 4/2007 | Lee ................................. 359/443 |
| 2010/0087883 | A1 * | 4/2010 | Sullivan et al. .................... 607/5 |

FOREIGN PATENT DOCUMENTS

WO     WO 2004/096027     11/2004

OTHER PUBLICATIONS

U.S. Appl. No. 12/821,617, filed Jun. 23, 2010, Yamagishi, et al.

* cited by examiner

*Primary Examiner* — John B Strege
(74) *Attorney, Agent, or Firm* — Oblon, Spivak, McClelland, Maier & Neustadt, L.L.P.

(57) ABSTRACT

An extraction unit extracts observation information and site information of a sample associated with the observation information from at least information on an image scanning report including an image scanning result of a medical image of the sample obtained by inspection. A display control unit controls a display unit to display a schema imitating the shape of the sample and at least the observation information extracted corresponding to a position of the site in the schema.

13 Claims, 5 Drawing Sheets

APPARATUS AND METHOD OF DISPLAYING IMAGE SCANNING REPORT

CROSS-REFERENCE TO RELATED APPLICATIONS

This application is based upon and claims the benefit of priority from prior Japanese Patent Application No. 2006-080859, filed Mar. 23, 2006, the entire contents of which are incorporated herein by reference.

BACKGROUND OF THE INVENTION

1. Field of the Invention

The present invention relates to an apparatus and a method of displaying an image scanning report, the apparatus being disposed in, for example, each of diagnosis and treatment departments that requests inspection to display an image scanning report photographed by a radiological technologist and to display an image of an inspection part by, for example, a doctor in charge of the diagnosis and treatment department.

2. Description of the Related Art

Each of diagnosis and treatment departments of the internal medicine or surgical department, the circulatory organ department and the like has been installed in medical facilities. A doctor in charge of each diagnosis and treatment department requests a radiation photographing such as X-ray photographing with respect to a sample, for example, a patient to a roentgenology and requests the physiology inspection that inspects blood and urine, the pathology inspection, the endoscope inspection and the like to each of inspection departments. The radiological technologist describes an image scanning report about, for example, an X-ray image or an endoscope image in each inspection department. The image scanning report is described by, for example, a file of text type.

An image scanning apparatus is provided in each diagnosis and treatment department. The image scanning apparatus of images displays, for example, the X-ray image or the endoscope image as a result of the inspection and also displays the image scanning report described by the radiological technologist. The doctor in charge of each diagnosis and treatment department displays, for example, the X-ray image or the endoscope image and also displays the image scanning report by manipulating the image scanning apparatus. It is necessary that the doctor in charge observes, for example, the X-ray image or the endoscope image displayed on the image scanning apparatus to rapidly comprehend the symptoms of patients by reading the image scanning report.

However, the radiological technologist who describes the image scanning report and the doctor in charge who reads the image scanning report are different person. The descriptive content of the image scanning report may be a distinctive sentence expression and a tedious sentence expression of the radiological technologist. For this reason, the doctor in charge understands the content of the image scanning report by mistake and may require time until the content of the image scanning report is accurately comprehended.

BRIEF SUMMARY OF THE INVENTION

An advantage of some aspects of the invention is that it provides an apparatus and a method of displaying an image scanning report, the apparatus capable of visually and intuitively comprehending the content of the image scanning report with accuracy.

According to a first aspect of the invention, there is provided an apparatus for displaying an image scanning report, including: an extraction unit for extracting observation information and site information of a sample associated with the observation information from at least information on the image scanning report including image scanning results of a medical image of the sample obtained by inspection; a display unit for displaying information on the basis of the information on the image scanning report; and a display control unit for controlling the display unit to display a schema imitating the shape of the sample and at least the observation information corresponding to a position of the site in the schema.

According to a second aspect of the invention, there is provided a method of displaying an image scanning report, including the steps of: extracting observation information and site information of a sample associated with the observation information from at least information on the image scanning report including an image scanning result of a medical image of the sample obtained by inspection; and displaying a schema imitating the shape of the sample on a display unit and displaying at least the observation information corresponding to a position of the site in the schema on the display unit.

DETAILED DESCRIPTION OF THE INVENTION

Preferred embodiments of the invention will be described hereinafter with reference to the accompanying drawings.

Figure 1:
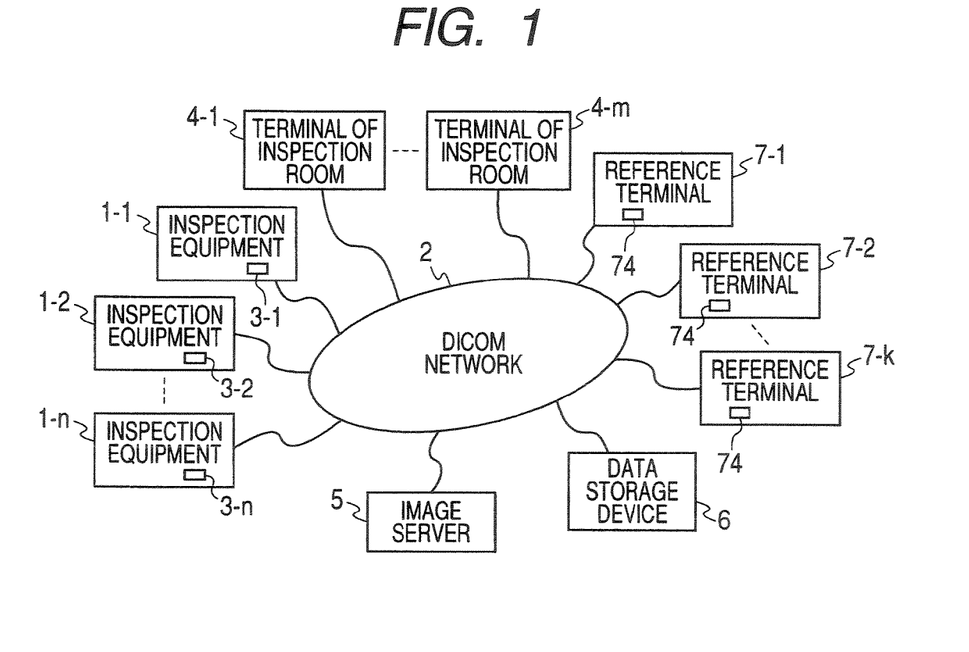
FIG. 1 is a configuration diagram showing a medical image management system including an apparatus for displaying an image scanning report according to an embodiment of the invention.

FIG. 1 is a configuration diagram showing a medical image management system including an apparatus for displaying an image scanning report. For example, various inspection equipments 1-1 to 1-$n$ are provided in each inspection room of medical care facilities, respectively. Each of the inspection equipment 1-1 to 1-$n$ includes, for example, X-ray CT device, MR device, ultrasonic inspection device, endoscope, digital-radiography, angiography device or the like. Each of the inspection equipment 1-1 to 1-$n$ obtains each inspection image data of the sample such as a human body, respectively. Each of the inspection equipment 1-1 to 1-$n$ is connected to DICOM (Digital Imaging and Communications in Medicine)

network 2. Each of the inspection equipment 1-1 to 1-n transmits each of the obtained inspection image data to the DICOM network 2.

Each terminal 3-1 to 3-n for inputting the image scanning report is installed in each inspection room. Each terminal 3-1 to 3-n for inputting the image scanning report is connected to the DICOM network 2. The image scanning report is inputted to each terminal 3-1 to 3-n for inputting the image scanning report by a manipulation of the radiological technologist. Each terminal 3-1 to 3-n for inputting the image scanning report transmits the information on the inputted image scanning report to the DICOM network 2.

A plurality of inspection rooms are installed in the medical care facilities. For example, pathology inspection or physiology inspection for inspecting blood or urine, nuclear medicine inspection (NM) or the like is conducted in each inspection room. Each terminal 4-1 to 4-m of the inspection rooms is installed in each inspection room. The inspection report about inspection results of, for example, pathology inspection or physiology inspection, nuclear medicine inspection (NM) or the like is inputted to each terminal 4-1 to 4-m of the inspection rooms by a manipulation of, for example, an inspection staff. Each terminal 4-1 to 4-m of inspection rooms is connected to the DICOM network 2. Each terminal 4-1 to 4-m of inspection rooms transmits the information on the inputted image scanning report to the DICOM network 2.

An image server 5 is connected to the DICOM network 2. The image server 5 stores medical image data or the like. For example, the image server 5 inputs each inspection image data from each inspection equipment 1-1 to 1-n through the DICOM network 2 and stores each inspection image data to be inputted. Each inspection image data obtained by the nuclear medicine inspection (NM) conducted in each inspection room is transmitted to the DICOM network 2 by manipulating each terminal 4-1 to 4-m of the inspection rooms. The image server 5 inputs each inspection image data obtained by the nuclear medicine (NM) through the DICOM network 2 and stores each inspection image data to be inputted.

A data storage device 6 is connected to the DICOM network 2. The data storage device 6 stores the information on the image scanning report inputted from each terminal 3-1 to 3-n for inputting the image scanning report. The data storage device 6 stores the information on the inspection report inputted from each terminal 4-1 to 4-m of the inspection rooms.

The information on the image scanning report and the information on the inspection report are filed by each free text type of, for example, DICOM—SR type or XML type.

Figure 2:
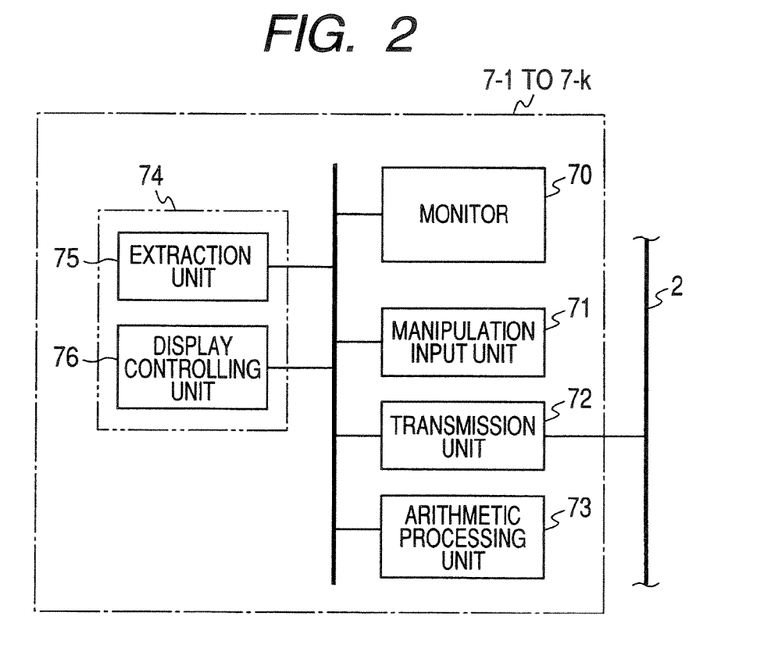
FIG. 2 is a block configuration diagram of each reference terminal in the apparatus according to the embodiment of the invention.

A plurality of medical examination rooms are installed in the medical care facilities. Each reference terminal 7-1 to 7-k is provided in each medical examination room. FIG. 2 is a block configuration diagram of each reference terminal 7-1 to 7-k. Each reference terminal 7-1 to 7-k has a monitor 70, a manipulation input unit 71 such as a keyboard and a mouse serving as an input unit, a transmission unit 72, an arithmetic processing unit 73, and an image scanning processing unit 74.

The transmission unit 72 is connected to the DICOM network 2. The transmission unit 72 transmits the data from each of the inspection equipments 1-1 to 1-n, each of the terminals 3-1 to 3-m for inputting the image scanning report, each of the terminals 4-1 to 4-m of the inspection room, the image server 5, and the data storage device 6 through the DICOM network 2.

The arithmetic processing unit 73 includes CPU, RAM, ROM or the like. The arithmetic processing unit 73 receives a manipulating instruction inputted from the manipulation input unit 71, operatively controls the transmission unit 72 and the image scanning processing unit 74, and display-controls the monitor 70. For example, the arithmetic processing unit 73 processes the display onto the monitor 70 based on the manipulation instruction inputted from the manipulation input unit 71.

Each of the reference terminals 7-1 to 7-k displays each of the inspection image data obtained by each of the inspection equipments 1-1 to 1-n on the monitor 70. Each of the reference terminals 7-1 to 7-k displays the information on each image scanning report inputted from each of the terminals 3-1 to 3-n for inputting the image scanning report on the monitor 70. Each of the reference terminals 7-1 to 7-k displays the information on the inspection report inputted from each of the terminals 4-1 to 4-m of the inspection room on the monitor 70.

The image scanning processing unit 74 displays the information on the image scanning report of various inspection items described with respect to the sample on the monitor 70. Moreover, the image scanning processing unit 74 also displays each of the inspection image data obtained by each of the inspection equipments 1-1 to 1-n on the monitor 70.

Specifically, the image scanning processing unit 74 has an extraction unit 75 and a display control unit 76. The extraction unit 75 receives the information on each of the image scanning reports inputted from each of the terminals 3-1 to 3-n for inputting the image scanning report and the information on the inspection report inputted from each of the terminals 4-1 to 4-m of the inspection room. The extraction unit 75 extracts observation information from the information on the received image scanning report and the information on the inspection report and site information of the sample according to this observation information. The observation information is a medical condition of the sample and includes, for example, a bloodstream drop, a simple fracture, and a shadow. The site information of the sample is a site presenting the medical condition of the sample and includes, for example, a left temporal lobe, a left parietal lobe, a left femur, and liver.

For example, the extraction unit 75 extracts the observation information and the site information on the medical condition or the site of the sample from the information on the image scanning report and the information on the inspection report. In addition, the extraction unit 75 processes the association (link) between the observation information and the site information. As a result of the association between the observation information and the site information, for example, the data having a layered structure of the observation information and the site information are configured.

For example, the extraction of the observation information and the site information of the sample utilizes text mining approach. After disassembling the information on the image scanning report and the information on the inspection report into each word level, the extraction of the observation information and the site information of the sample is performed by extracting the observation information that includes, for example, the bloodstream drop, the simple fracture, and the shadow and the site information that includes, for example, the left temporal lobe, the left parietal lobe, the left femur, and the liver from the sentence of the disassembled word levels. Then, for example, the association between the bloodstream drop as the observation information and the left temporal lobe as the site information is performed. Moreover, the association between the simple fracture as the observation information and the left femur as the site information is performed.

Figure 3:
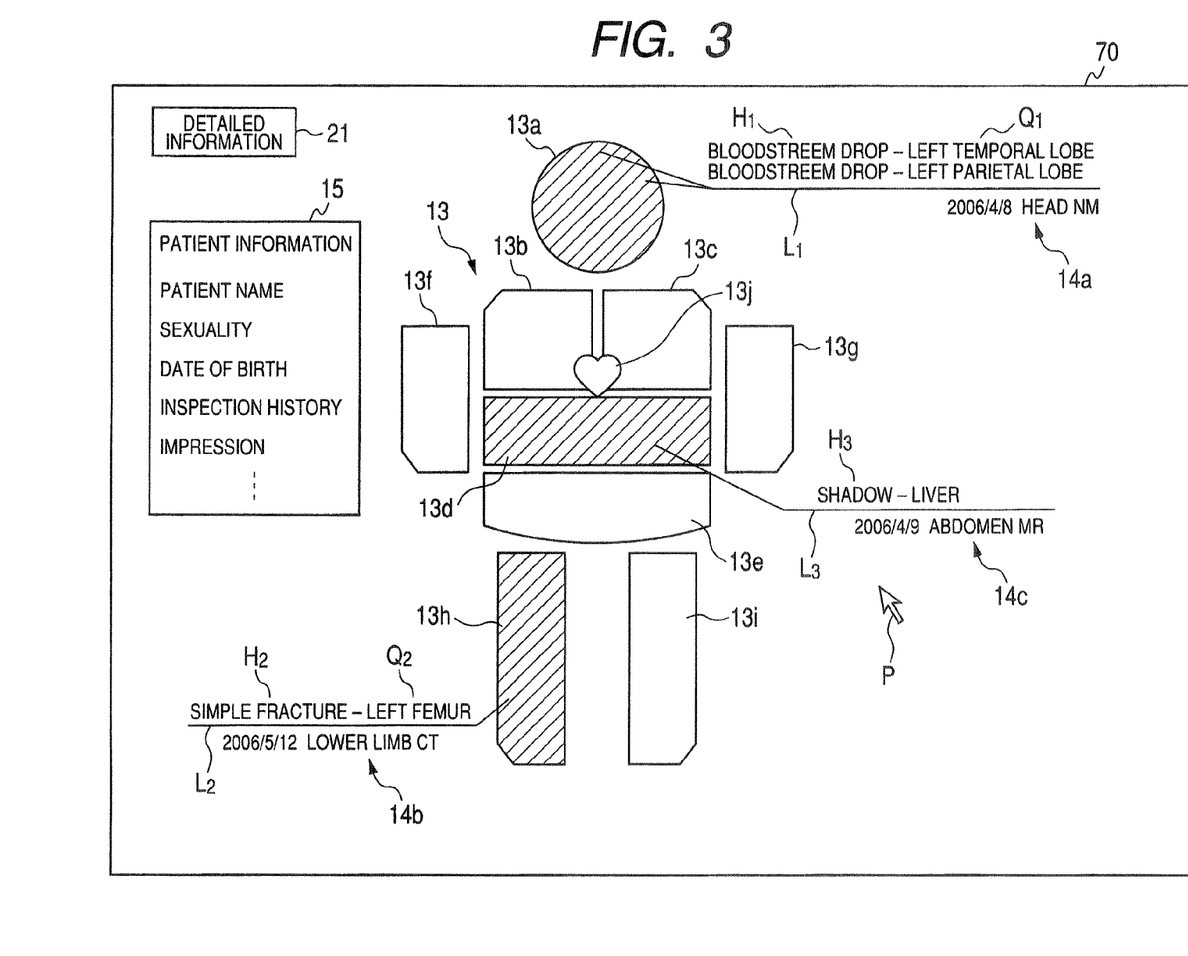
FIG. 3 is a view showing a display example of observation information and site information on schema that is imitated as a shape of human body in the apparatus according to the embodiment of the invention.

The display control unit 76 displays a diagram imitating the shape of the sample on the each monitor 70 of each of the reference terminals 7-1 to 7-k, as shown in FIG. 3. The diagram is a schema 13 imitating a shape of human body. A schema 13 is formed of, for example, a head 13a, a left thorax 13b, a right thorax 13c, an abdomen 13d, a lower abdomen 13e, a left arm 13f, a right arm 13g, a left leg 13h, a right leg 13i, and a heart 13j. The schema 13 is not limited to form by dividing each site as shown in FIG. 3, but may be formed by dividing the human body into arbitrary sites.

The display control unit 76 receives the observation information extracted by the extraction unit 75 and the site information of the sample to display the observation information and the site information in response to the position of each site on the schema 13. The observation information and the site information are associated with each other by the extraction unit 75. The display control unit 76 displays the observation information and the site information associated with each other on the monitor 70.

Specifically, the display control unit 76 displays, for example, "bloodstream drop—left temporal lobe" that is the association between the bloodstream drop as the observation information $H_1$ and the left temporal lobe as the site information $Q_1$ on the monitor 70 in response to the position of the head 13a, as shown in FIG. 3. The display control unit 76 displays a drawing line $L_1$ extending from the head 13a and displays "bloodstream drop—left temporal lobe" on the drawing line $L_1$.

Hereinafter, likewise, the display control unit 76 displays, for example, "bloodstream drop—left parietal lobe" as the observation information $H_1$—the site information $Q_1$ in response to the position of the head 13a. The head 13a presents two medical condition of "bloodstream drop—left temporal lobe" and "bloodstream drop—left parietal lobe." The display control unit 76 displays, for example, "simple fracture—left femur" as the observation information $H_2$—the site information $Q_2$ in response to the position of the left leg 13h. The display control unit 76 displays a drawing line $L_2$ extending from the left leg 13h and displays "simple fracture—left femur" on the drawing line $L_2$. The display control unit 76 displays, for example, "shadow—liver" as the observation information $H_3$—the site information $Q_3$ in response to the position of the abdomen 13d. The display control unit 76 displays a drawing line $L_3$ extending from the abdomen 13d and displays "shadow—liver" on the drawing line $L_3$.

The display control unit 76 appends an inspection date and time "year/month/date" and each information 14a to 14c on the image inspection of medical instruments or the like used in the inspection to each observation information $H_1$ to $H_3$ and each site information $Q_1$ to $Q_3$ to display on the monitor 70. The information 14a to 14c on the image inspection is displayed in parallel to the observation information $H_1$ to $H_3$ and the site information $Q_1$ to $Q_3$, respectively. The information 14a to 14c on the image inspection is displayed below the drawing lines $L_1$ to $L_3$, respectively. For example, the information on the image inspection 14a represents the inspection date and time "2006 Apr. 8" and "nuclear medicine inspection (NM) for the head." Likewise, the information on the image inspection 14b represents the inspection date and time "2006 May 12" and "X-ray CT for the lower limb." The information on the image inspection 14c represents the inspection date and time "2006 Apr. 9" and "MR for the abdomen."

The display control unit 76 can change a display color of each site on the schema 13 based on the level of importance of each observation information $H_1$ to $H_3$. For example, in the case where the medical condition deteriorates or the emergency state is required according to the content described in the observation information $H_1$ to $H_3$ and the site information $Q_1$ to $Q_3$, the display control unit 76 displays the display color of each site on the schema 13 by, for example, "red." The display control unit 76 can blink the display color of each site on the schema 13, for example, the display color such as a "red" and the like. For example, each medical condition is preliminarily divided into two or more groups based on the heaviness and lightness of the medical condition. The display color of the site on the schema 13 is set in every group. Accordingly, the display control unit 76 determines the display color of each site on the schema 13 according to the content described in the observation information $H_1$ to $H_3$ and the site information $Q_1$ to $Q_3$.

For instance, as shown in FIG. 3, the head 13a shows the medical condition of "bloodstream drop—left parietal lobe." For this reason, the display control unit 76 displays the display color of the head 13a by, for example, "yellow." Likewise, the left leg 13h shows the medical condition of "simple fracture—left femur." For this reason, the display control unit 76 displays the display color of the left leg 13h by, for example, "yellow." The abdomen 13d shows the medical condition of "shadow—liver." For this reason, the display control unit 76 displays the display color of the abdomen 13d by, for example, "yellow."

The display control unit 76 displays patient information 15 on the monitor 70. The patient information 15 is located so as to be adjacent to the schema 13 on the display screen of the monitor 70. The patient information 15 includes, for example, patient name, sexuality, date of birth, inspection history, and impression.

Figure 4:
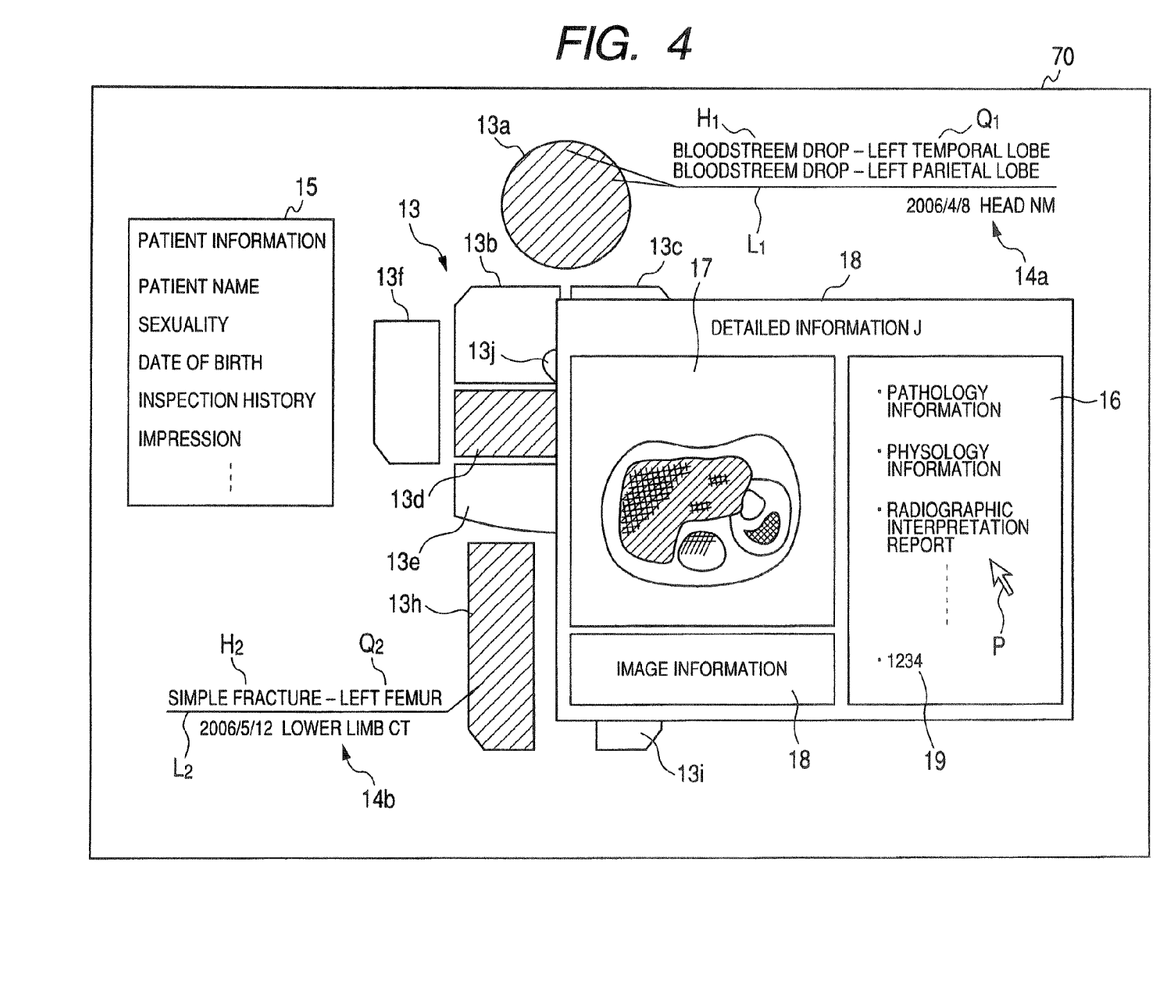
FIG. 4 is a view showing a display example of information and inspection image data of inspection items on the schema in the apparatus according to the embodiment of the invention.

As shown in FIG. 4, if the display area including the observation information $H_1$ to $H_3$ and the site information $Q_1$ to $Q_3$ on the schema 13 displayed on the monitor 70 is designated, the display control unit 76 displays detailed information J corresponding to the designated site on the monitor 70.

The detailed information J has the information 16 on various inspection items and inspection image data 17. The information 16 on various inspection items includes, for example, pathology information, physiology information, and each item of image scanning report by MR. The inspection image data 17 includes each of the inspection image data obtained by each of the inspection equipment 1-1 to 1-n.

Specifically, for example, the display control unit 76 receives the manipulation of the mouse in manipulation input unit 71 and moves pointer P onto the display screen of the monitor 70 according to the mouse manipulation. When the pointer P is moved onto the display area including the observation information $H_1$ to $H_3$ and the site information $Q_1$ to $Q_3$ on the schema 13, the display control unit 76 displays a detailed information window 18 on the monitor 70. The display area including the observation information $H_1$ to $H_3$ and the site information $Q_1$ to $Q_3$ is the area from the display area of the observation information $H_1$ to $H_3$ and the site information $Q_1$ to $Q_3$ to the distance set beforehand.

When the pointer P is moved onto the display area including, for example, "shadow—liver/Apr. 9, 2006, MR for the abdomen", the display control unit 76 displays the detailed information window 18 on the monitor 70. Moreover, the display control unit 76 displays the MR image scanning report 16 within the detailed information window 18 and displays MR image 17 by starting the image scanning viewer. That is, the display control unit 76 links between the display area including, for example, the observation information $H_3$ such as "shadow—liver/Apr. 9, 2006, MR for the abdomen" and the site information $Q_3$ on the display screen of the monitor 70 and the inspection image data of the MR image 17. For this reason, when the pointer P is moved onto the display area including "shadow—liver/Apr. 9, 2006, MR for the abdomen" on the schema 13, the display control unit 76 can read the inspection image data of the MR image 17 or the like.

In this case, for example, the display control unit 76 reads the inspection image data of the MR image 17 or the like from the image server 5 to display on the monitor 70 of each reference terminal 7-1 to 7-k through the DICOM network 2. Specifically, for example, the display control unit 76 conducts Query/Retrieve (search and reference of the image) by using the key of SOP instance UID as an address capable of specifying the inspection image data of the MR image 17. For this reason, for example, the display control unit 76 obtains the inspection image data of the MR image 17 from the image server 5. For instance, patient name, patient ID, inspection date, and inspection ID are used as the key of the SOP instance UID for searching.

The display control unit 76 can change the display position of the detailed information window 18 on the display screen of the monitor 70 according to the site of the observation information and the site information on the schema 13. For example, if "shadow—liver/Apr. 9, 2006, MR for the abdomen" is selected, the display control unit 76 displays the detailed information window 18 at the screen position on the monitor 70 corresponding to the abdomen 13d on the schema 13.

The display control unit 76 may display image information 17a of the inspection image data in the MR image 17 and numerical information 19 within the detailed information window 18. The numerical information 19 is numerical values of various inspection results extracted from, for example, the information on the image scanning report and the information on the inspection report by, for example, the extraction unit 75. The numerical information 19 is, for instance, an amount of protein in the urine test.

Figure 5:
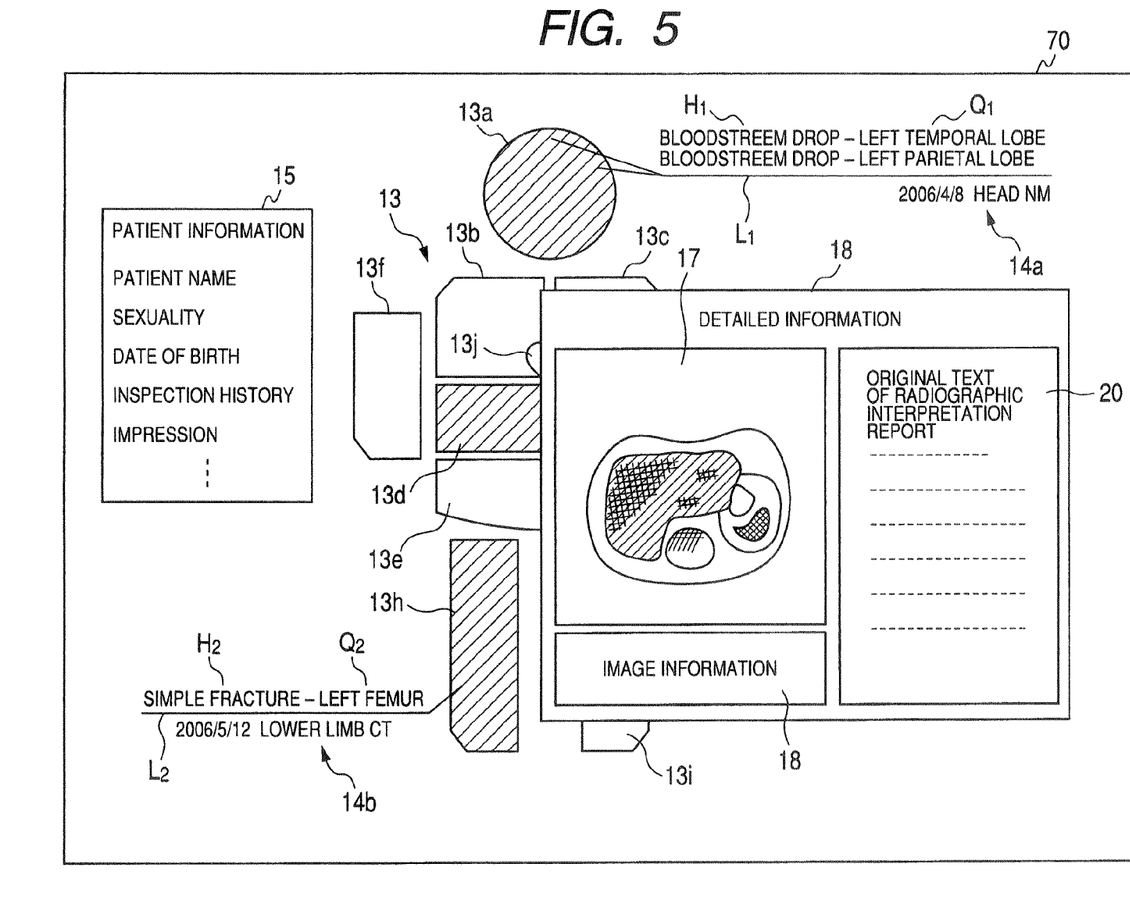
FIG. 5 is a view showing a display example of an original text of information on the image scanning report or inspection report in the apparatus according to the embodiment of the invention.

When the pointer P is moved onto, for example, the image scanning report among the information 16 on various inspection items shown in FIG. 4 and the image scanning report is designated by clicking (or double clicking) the mouse under such a state, the display control unit 76 displays the original text 20 of the information on the image scanning report and the information on the inspection report corresponding to the designated inspection item within the detailed information window 18, as shown in FIG. 5. In this case, as shown in FIG. 5, the display control unit 76 displays the original text 20 of the information on the image scanning report and the information on the inspection report instead of the information 16 on various inspection items that are shown in FIG. 4.

The display control unit 76 displays a detailed information switch 21 serving as detailed information instructing unit on the monitor 70, as shown in FIG. 3. The detailed information switch 21 is a switch for displaying the original text 20 of either of the information on the image scanning report and the information on the inspection report corresponding to, for example, the observation information $H_1$ to $H_3$ on the monitor 70.

If the detailed information switch 21 shown in FIG. 3 is clicked (or double clicked) and the pointer P is onto the observation information $H_3$ and the site information $Q_3$ to be clicked (or to be double clicked), the display control unit 76 displays the original text 20 of the information on the image scanning report and the information on the inspection report corresponding to the observation information $H_3$ and the site information $Q_3$ on the monitor 70, as shown in FIG. 5.

Figure 6:
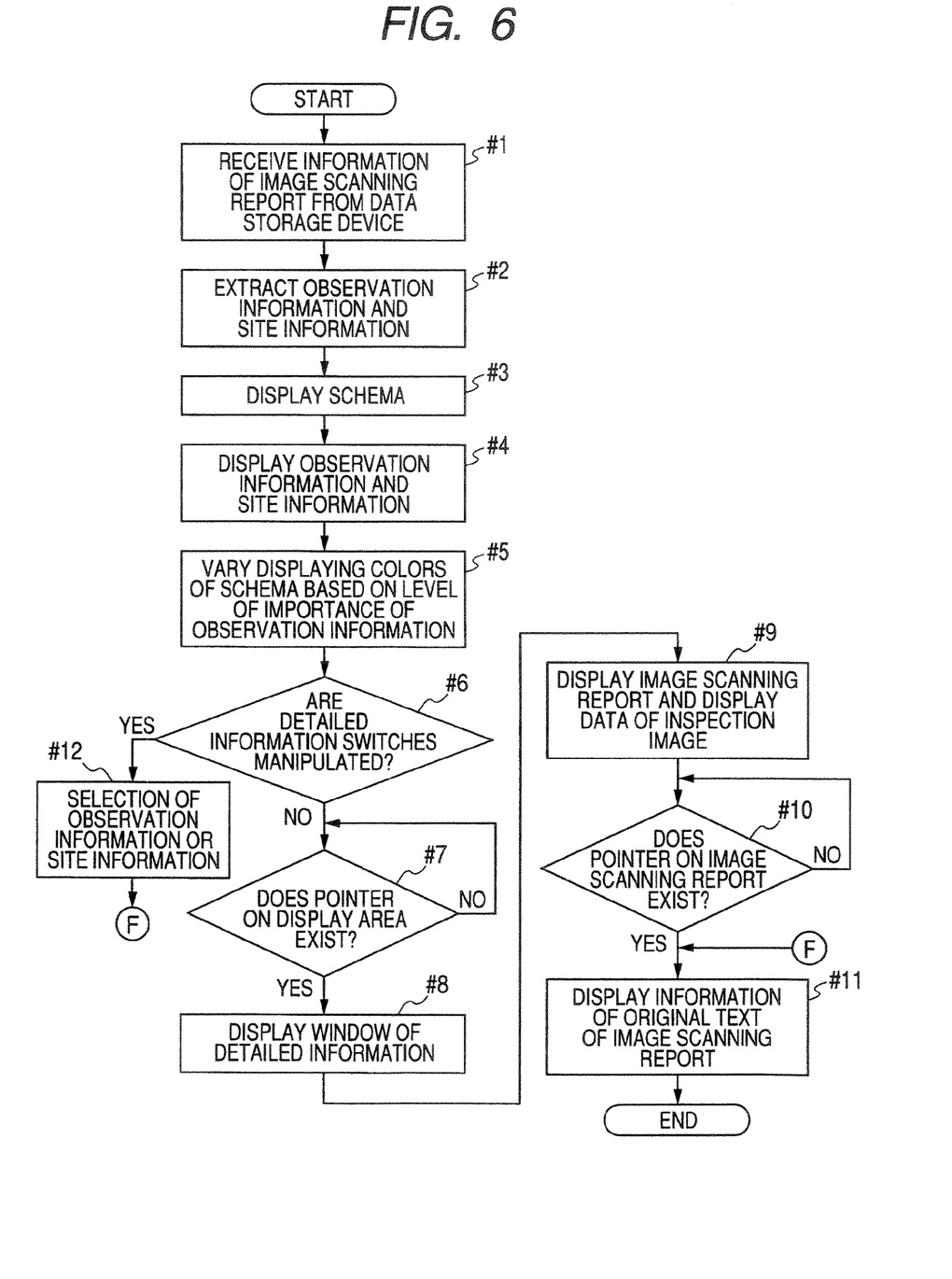
FIG. 6 is a flowchart showing a process of the image scanning in the apparatus according to the embodiment of the invention.

Next, a process of the image scanning by the apparatus configured as described above will be described with reference to the flowchart of an image scanning process shown in FIG. 6.

The photography of the sample such as the patient with MR device is required to the inspection room by the doctor in charge of the medical examination room. For example, the MR image 17 of liver of the sample is photographed by MR device in the inspection room. The radiological technologist observes the MR image 17 of, for example, liver and inputs the image scanning report through the image scanning report inputting terminal 3-1.

When the photography of the MR image 17 and the input of the image scanning report are terminated, the inspection equipment 1-1 that serves as MR device transmits the MR image data as an instruction image data to the image server 5 through the DICOM network 2. For this reason, the image server 5 stores, for example, the MR image data of the liver of the patient. In addition to the patient information 15 of, for example, patient name, sexuality, date of birth, inspection history, and impression, the information on the inspection date and time "Apr. 9, 2006" and the MR photography for the abdomen is added to the MR image data.

The image scanning report inputting terminal 3-1 transmits the information on the image scanning report to the data storage device 6 through the DICOM network 2. For this reason, for example, the data storage device 6 stores the information on the image scanning report with respect to the MR image data of the liver. The patient information 15 of, for example, patient name, sexuality, date of birth, inspection history, and impression is added to the information on the image scanning report.

The extraction unit 75 receives the information on the image scanning report stored in the data storage device 6 through the DICOM network 2 in step #1.

Next, the extraction unit 75 extracts the observation information and the site information described in the received information on the image scanning report in step #2. For example, the extraction unit 75 extracts the shadow as the observation information $H_3$. The extraction unit 75 extracts the liver as the site information $Q_3$. The extraction unit 75 conducts the association between the shadow and the liver and configures the data having the layered structure of the observation information $H_3$ and the site information $Q_3$.

Meanwhile, for example, the doctor in charge of the medical examination room manipulates the reference terminal 7-1 so as to observe the required MR image. In step #3, the display control unit 76 receives the instruction from the reference terminal 7-1 and displays the schema 13 imitating the shape of the human body on the display screen of the monitor 70 shown in FIG. 3. Moreover, the display control unit 76 displays, for example, the observation information $H_1$ to $H_3$ and the site information $Q_1$ to $Q_3$ on the schema 13 extracted by the extraction unit 75 in step #4. For example, the display control unit 76 displays the "shadow—liver" on the schema 13 corresponding to the position of the head 13a. At the same time, the display control unit 76 displays the inspection date and time "Apr. 9, 2006" and the "MR for the abdomen" so as to be in parallel to the "shadow—liver."

If there is the observation information besides "shadow—liver", the display control unit 76 displays simultaneously, for example, "bloodstream drop—left parietal lobe" corresponding to the position of the head 13a and "simple fracture—left femur" corresponding to the position of the left leg 13h, as shown in FIG. 3. The display control unit 76 displays the patient information 15, for example, patient name, sexuality, date of birth, inspection history, and impression on the monitor.

Next, the display control unit 76 can change the display color of each site on the schema 13 based on the level of importance of each observation information $H_1$ to $H_3$ in step #5. For example, when the head 13a shows the medical condition of "bloodstream drop—left parietal lobe", the display control unit 76 displays the display color of the head 13a by, for example, "yellow." When the abdomen 13d shows the medical condition of "shadow—liver", the display control unit 76 displays the display color of the abdomen 13*d* by, for example, "yellow."

Next, for example, the display control unit 76 determines whether or not the detailed information switch 21 shown in FIG. 3 is clicked (or double clicked) in step #6. As a result of the determination, if the detailed information switch 21 is not clicked (or double clicked), the display control unit 76 proceeds to the following step #7.

The doctor in charge moves the pointer P onto the display screen of the monitor 70 by manipulating the mouse. The display control unit 76 determines whether or not the pointer P is moved onto the display area including the observation information $H_1$ to $H_3$ and the site information $Q_1$ to $Q_3$ on the schema 13, that is, onto the display area including "shadow—liver/Apr. 9, 2006, MR for the abdomen" in step #7.

As a result of the determination, when the pointer P is moved onto the display area including "shadow—liver/Apr. 9, 2006, MR for the abdomen" on the schema 13, as shown in FIG. 4, the display control unit 76 displays the detailed information window 18 in step #8. At this time, the display control unit 76 displays the display position of the detailed information window 18 so as to correspond to the abdomen 13*d* in the schema 13 on the display screen of the monitor 70.

Next, the display control unit 76 displays, for example, "image scanning report" as the information 16 on various inspection items within the detailed information window 18 and displays the MR image 17 by starting an image scanning viewer in step #9. In this case, the display control unit 76 conducts Query/Retrieve (search and reference of the image) by using the key of SOP instance UID as an address capable of specifying the inspection image data of the MR image 17 and obtains the inspection image data of the MR image 17 from the image server 5 to display on the monitor 70.

If the information 16 on various inspection items includes, for example, the pathology information and the physiology information, the display control unit 76 displays the pathology information and the physiology information within the detailed information window 18.

Then, the doctor in charge of the medical examination room moves the pointer P onto the display screen of the monitor 70 by manipulating the mouse. The display control unit 76 determines whether or not the pointer P is moved onto the "image scanning report" serving as the information 16 on the inspection items in step #10 and the mouse is clicked (or double clicked).

As the results of the determinations, when the pointer P is moved onto, for example, the "image scanning report" and the mouse is clicked (or double clicked), the display control unit 76 displays the original text 20 of the "image scanning report", as shown in FIG. 5, instead of the information 16 on various inspection items that are shown in FIG. 4 within the detailed information window 18 in step #11. The original text 20 of the "image scanning report" means the image scanning report in which the radiological technologist observes the MR image 17 of the abdomen 13*d* presenting the medical condition of the "shadow—liver" to describe the content of the MR image 17.

When the pathology information and the physiology information are described, the display control unit 76 determines whether or not the pointer P is moved onto the pathology information and the physiology information and the mouse is clicked (or double clicked). As the results of the determinations, when the pointer P is moved onto the pathology information and the physiology information and the mouse is clicked (or double clicked), the display control unit 76 displays the original text 20 of the pathology information and the physiology information within the detailed information window 18.

Meanwhile, as the result of the determination in step #6, when the detailed information switch 21 shown in FIG. 3 is clicked (or double clicked), the process proceeds to step #12. In this case, the display control unit 76 waits to select either of the observation information $H_1$ to $H_3$ and the site information $Q_1$ to $Q_3$ displaying the detailed information J.

At this time, for example, when the pointer P is moved onto the observation information $H_3$ and the site information $Q_3$ to be clicked (or double clicked) by the mouse manipulation of the doctor in charge, the display control unit 76 determines that the observation information $H_3$ and the site information $Q_3$ are selected. Moreover, the process proceeds to step #11, and the display control unit 76 displays the detailed information window 18, as shown in FIG. 5. The detailed information window 18 includes the original text 20 of the "image scanning report" corresponding to the observation information $H_3$ and the site information $Q_3$. The original text 20 of the "image scanning report" means the image scanning report in which the radiological technologist observes the MR image 17 of the abdomen 13*d* presenting the medical condition of the "shadow—liver" to describe the content of the MR image 17.

The original text 20 of the "image scanning report" may be displayed by clicking (or double clicking) the detailed information switch 21 after the observation information $H_1$ to $H_3$ and the site information $Q_1$ to $Q_3$ are selected.

As described above, according to the embodiment of the invention, the observation information $H_1$ to $H_3$ and the site information $Q_1$ to $Q_3$ presenting the medical condition are extracted from the image scanning report, and the observation information $H_1$ to $H_3$ and the site information $Q_1$ to $Q_3$ are displayed on the monitor 70 so as to correspond to the position of each site on the schema 13 imitating the shape of the patient. When the display area of the observation information $H_1$ to $H_3$ and the site information $Q_1$ to $Q_3$ is designated by the pointer P, the information on various inspection items and the inspection image data corresponding to the designated site are displayed on the monitor 70. In addition, when the information on various inspection items is designated, the original text 20 of the information on the image scanning report corresponding to the inspection item is displayed on the monitor 70.

For this reason, even though the descriptive content of the image scanning report described by the radiologist technologist is a distinctive sentence expression and a tedious sentence expression, the observation information $H_1$ to $H_3$ and the site information $Q_1$ to $Q_3$ of the shadow or bloodstream drop, the simple fracture and the like showing the important medical condition on the schema 13 can be simultaneously seen. The doctor in charge can visually and intuitively diagnose the medical condition of the sample. As a result, the doctor in charge accurately diagnoses the medical condition of the patient and can shorten the time until the diagnostic result is given.

For example, on the schema 13, the display color of the head 13*a* showing the medical condition of the "bloodstream drop—left parietal lobe" is displayed by "yellow." The site of the human body presenting the medical condition can be visually understood only by seeing schema 13. In the case where the medical condition deteriorates or the emergency state is required, the display color of each site on the schema 13 is displayed by, for example, "red." The case where the medical deteriorates can be also visually understood by blinking the display color such as "red."

To know the detailed information J of the medical condition, the image scanning viewer of the inspection image data of, for example, MR image data 17 can be conducted by only moving the pointer P onto the observation information $H_1$ to $H_3$ and the site information $Q_1$ to $Q_3$ of the medical condition. The doctor in charge can diagnose the detailed state of the medical condition by seeing the inspection image data of MR image data 17.

Only by moving the pointer P onto the information 16 on the inspection item of the image scanning report or the like to click (or double click), the original text 20 of the image scanning report or the like can be displayed on the monitor 70. Accordingly, the original text of the image scanning report or the like can be also confirmed.

As previously described above, the observation information $H_1$ to $H_3$ and the site information $Q_1$ to $Q_3$ of the medical condition are displayed, and the inspection image data such as the MR image data 17 is displayed by the image scanning viewer. The doctor in charge never understands the content of original text 20 such as the image scanning report information by mistake. The doctor in charge will not require time until the content of original text 20 such as the image scanning report is accurately understood.

If the detailed information switch 21 is clicked (or double clicked), the original text 20 such as the image scanning report information or the inspection report information of the designated site in the sample is displayed on the monitor 70. That is, it is possible to move from the state where the schema 13 shown in FIG. 3 is displayed to the state where the original text 20 such as the image scanning report information or the inspection report information shown in FIG. 5 is displayed. For this reason, the charge medicine can immediately see the original text 20 such as the image scanning report information or the inspection report information on the site of the observation information $H_1$ to $H_3$ and the site information $Q_1$ to $Q_3$ presenting the anxious medical condition.

In addition, the invention is not limited to the embodiment as described above, but may be modified as follows.

The image scanning processing unit 74 is provided at each of the reference terminals 7-1 to 7-k. However, it is not limited thereto, and the image scanning processing unit 74 may be accessible to each of the reference terminals 7-1 to 7-k by directly connecting to the DICOM network 2.

For example, since the image scanning viewer determines an accession number showing the system number of the respective inspection equipments 1-1 to 1-n as the key of SOP instance UID, it may send the URL link information and may display with WEB base.

It may connect a hospital information system (HIS) 35 or a radiology information system (RIS) to the DICOM network 2.

The detailed information switch 21 is not limited to display on the display screen of the monitor 70. The detailed information switch 21 may be installed on the main body of the respective reference terminals 7-1 to 7-k by using a mechanical switch such as push-buttons.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An apparatus for displaying an image scanning report, comprising:
    an extraction unit for extracting a first character string showing a medical condition of a sample and a second character string showing a site presenting the medical condition from the image scanning report, including image scanning results of a medical image of the sample obtained by inspection as a character string, and associating the first character string with the second character string;
    a display unit for displaying information on the basis of the image scanning report; and
    a display control unit for displaying a schema imitating the shape of the sample on the display unit, and for displaying the first character string and the second character string associated with the first character string at a position corresponding to the site in the schema on the display unit.

2. The apparatus according to claim 1, further comprising an input unit for designating a display area including the position of the site in the schema or the first character string displayed on the display unit,
    wherein the display control unit displays information on various inspection items associated with a position of the sample designated by the input unit or the medical image on the display unit.

3. The apparatus according to claim 2, wherein the input unit can designate the information on various inspection items displayed on the display unit, and
    wherein the display control unit displays the information on the image scanning report corresponding to the information on the inspection item designated by the input unit on the display unit.

4. The apparatus according to claim 1, wherein the display control unit can change a display color of the schema based on the level of importance of the first character string.

5. The apparatus according to claim 1, wherein the display control unit displays additively inspection date and time or at least one of information on medical instruments used in the inspection on the display unit.

6. The apparatus according to claim 2, wherein the display control unit links the second character string with the medical image of the site and reads the medical image to display on the display unit when the display area, including the first character string and the second character string, is designated on a display screen of the display unit.

7. The apparatus according to claim 2, wherein the display control unit can change the information on the inspection item and a display position of the medical image on the schema in response to the first character string and the second character string on the schema.

8. The apparatus according to claim 2, wherein the display control unit displays the information of the inspection item and the medical image on the display unit, when a pointer is moved onto the display area including the first character string and the second character string on the schema.

9. The apparatus according to claim 3, wherein the display control unit displays the information on the image scanning report on the display unit, when a pointer is moved onto the information on the inspection item and is clicked at least once.

10. The apparatus according to claim 1, further comprising a detailed information instructing unit for displaying the information on the image scanning report,
    wherein the display control unit displays at least information on the image scanning report corresponding to the first character string on the display unit at the state where the schema is displayed on the display unit, when there is a display designation of the information on the image scanning report from the detailed information instructing unit.

11. A method of displaying an image scanning report, comprising:
  extracting, via an extraction unit, a first character string showing a medical condition of a sample and a second character string showing a site presenting the medical condition from the image scanning report, including image scanning results of a medical image of the sample obtained by inspection as a character string; and
  displaying, via a display unit, information on the basis of the image scanning report; and
  controlling, via a display control unit, the display of a schema imitating the shape of the sample on the display unit, and the display of the first character string and the second character string associated with the first character string at a position corresponding to the site in the schema on the display unit.

12. The method according to claim 11, wherein information on various inspection items related to the position of the sample designated or the medical image is displayed on the display unit, when a display area including the position of the site on the schema or the first character string displayed on the display unit is designated.

13. The method according to claim 12, wherein the information on the image scanning report corresponding to the information on the designated inspection item is displayed on the display unit, when the information of various inspection items displayed on the display unit is designated.

* * * * *